(12) United States Patent
Gutel et al.

(10) Patent No.: US 10,305,091 B2
(45) Date of Patent: May 28, 2019

(54) MATERIAL FOR AN ELECTRODE OF AN ORGANIC BATTERY COMPRISING BENZENE-BIS(DITHIOIC) ACID DERIVATIVES

(71) Applicant: COMMISSARIAT À L'ENERGIE ATOMIQUE ET AUX ENERGIES ALTERNATIVES, Paris (FR)

(72) Inventors: Thibaut Gutel, Veurey-Voroize (FR); Lionel Dubois, Verrens-Arvey (FR); Adriana Iordache, Grenoble (FR)

(73) Assignee: COMMISSARIAT À L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 53 days.

(21) Appl. No.: 15/033,658

(22) PCT Filed: Oct. 29, 2014

(86) PCT No.: PCT/IB2014/065682
§ 371 (c)(1),
(2) Date: May 2, 2016

(87) PCT Pub. No.: WO2015/063697
PCT Pub. Date: May 7, 2015

(65) Prior Publication Data
US 2016/0254531 A1    Sep. 1, 2016

(30) Foreign Application Priority Data
Oct. 30, 2013 (FR) ..................... 13 60611

(51) Int. Cl.
| | |
|---|---|
| C07C 327/18 | (2006.01) |
| H01M 4/04 | (2006.01) |
| H01M 4/62 | (2006.01) |
| H01M 4/137 | (2010.01) |
| H01M 10/0525 | (2010.01) |
| H01M 10/054 | (2010.01) |
| H01M 4/1399 | (2010.01) |
| H01M 4/60 | (2006.01) |
| H01M 10/052 | (2010.01) |
| H01B 1/12 | (2006.01) |
| C09D 5/44 | (2006.01) |
| C25D 13/16 | (2006.01) |

(52) U.S. Cl.
CPC .......... *H01M 4/137* (2013.01); *C07C 327/18* (2013.01); *C09D 5/4476* (2013.01); *C25D 13/16* (2013.01); *H01B 1/122* (2013.01); *H01M 4/0402* (2013.01); *H01M 4/0404* (2013.01); *H01M 4/0411* (2013.01); *H01M 4/0466* (2013.01); *H01M 4/1399* (2013.01); *H01M 4/60* (2013.01); *H01M 4/602* (2013.01); *H01M 4/608* (2013.01); *H01M 4/623* (2013.01); *H01M 4/625* (2013.01); *H01M 10/052* (2013.01); *H01M 10/054* (2013.01); *H01M 10/0525* (2013.01)

(58) Field of Classification Search
None
See application file for complete search history.

(56) References Cited

U.S. PATENT DOCUMENTS

| | | | |
|---|---|---|---|
| 7,651,647 | B1 | 1/2010 | Strange et al. |
| 2005/0239917 | A1 | 10/2005 | Nelson et al. |
| 2009/0152509 | A1 | 6/2009 | Choi et al. |
| 2009/0181309 | A1 | 7/2009 | Kwon et al. |
| 2012/0258360 | A1 | 10/2012 | Ogihara |

FOREIGN PATENT DOCUMENTS

| | | |
|---|---|---|
| EP | 1244168 A1 | 9/2002 |
| JP | 2008-192452 A | 8/2008 |
| WO | 98/01478 A1 | 1/1998 |
| WO | 2009/043729 A2 | 4/2009 |
| WO | 2009-127674 A1 | 10/2009 |

OTHER PUBLICATIONS

Yangjun Xing et al., "Optimizing Single-Molecule Conductivity of Conjugated Organic Oligomers with Carbodithioate Linker," Journal of the American Chemical Society, Jun. 16, 2010, vol. 132, No. 23.

Eleftheria Neofotistou et al., "Novel Coordination Polymers Based on the Tetrathioterephthalate Dianion as the Bridging Ligand," Inorganic Chemistry, Oct. 1, 2007, vol. 46, No. 21, pp. 8487-8489.

Alok R. Paital et al., "Synthesis and structures of perthio- and polymeric metal complexes with the tetrathio- and dithioterephthalate ligands," Polyhedron, Jun. 22, 2013, vol. 64, pp. 328-338.

Y Ueno et al., "Tetrathioquinodimethane chemistry. A new approach to the preparation of charge-transfer complex by lithium iodide reduction", Tetrahedron Letters, Jan. 1, 1977, pp. 4607-4610.

M. Armand et al. "Conjugated dicarboxylate anodes for Li-ion batteries," Nature Materials, Feb. 1, 2009, vol. 8, pp. 120-125.

Wudle F et al. "Recent advances in the synthesis of octathioquinodimethan (OTQ) culminating in the preparation of a perthiomethylated terephthalate, a methylated precursor of OTQ are presented," Molecular Crystals and Liquid crystals, Taylor & Francis, UK, vol. 125, Jan. 1, 1985, pp. 181-189.

(Continued)

*Primary Examiner* — Tanisha Diggs
(74) *Attorney, Agent, or Firm* — Oliff PLC (57) ABSTRACT

The present invention concerns the use, as an active electrode material, of compounds comprising at least one entity of formula (I): in which the phenyl group is substituted with one to four identical or different substituent(s) R, chosen from a hydrogen atom, a halogen atom chosen from fluorine, chlorine, bromine or iodine, a —C(=S)—S—C+ group, an —O—C+ group, an —S—C+ group, C+ being an alkali cation chosen from Li+, Na+ and K+, a (C1-C12) alkyl radical, a (C2-C12) alkenyl radical, a (C6-C14) aryl or heteroaryl radical; or two vicinal substituents R that can, if appropriate, be linked to each other to together form a 3- to 7-membered ring optionally including another heteroatom chosen from N, O or S; in the base or salt form; and the tautomeric forms of same. It also concerns an electrode material, an electrode and a lithium, sodium or potassium secondary battery, obtained from these compounds.

16 Claims, 7 Drawing Sheets

(56) References Cited

OTHER PUBLICATIONS

Feb. 19, 2015 International Search Report issued in International Patent Application No. PCT/IB2014/065682.
Jul. 11, 2014 French Search Report and Written Opinion issued in French Preliminary Search Report FR1360611.

MATERIAL FOR AN ELECTRODE OF AN ORGANIC BATTERY COMPRISING BENZENE-BIS(DITHIOIC) ACID DERIVATIVES

The present invention relates to the field of lithium, sodium or potassium storage batteries. It is targeted more particularly at providing a novel electrode active material for these storage batteries and in particular for lithium-ion batteries.

Lithium batteries are increasingly used as autonomous energy sources, in particular in portable devices, where they are gradually replacing nickel-cadmium (NiCd) and nickel-metal hydride (NiMH) batteries. This change is explained by the continuous improvement in the performances of lithium batteries, thus conferring on them energy densities which are markedly greater than those provided by the NiCd and NiMH product lines. Lithium batteries find multiple applications, in particular in new information and communication technologies (NICTs), medical devices, electric vehicles, the storage of the energy of photovoltaic cells, and the like.

These lithium electrochemical generators operate conventionally on the principle of insertion or deinsertion (or intercalation-deintercalation) of lithium on at least one electrode. In particular, in a lithium-ion battery, the $Li^+$ cations thus move back and forth between the respectively positive and negative electrodes, at each charging and discharging of the battery. The active material of the positive electrode is capable of releasing lithium ions at the time of charging and of incorporating lithium ions at the time of discharging.

Generally, the electrode active compounds used in commercial batteries are, for the positive electrode, lamellar compounds, such as $LiCoO_2$, $LiNiO_2$ and mixed compounds $Li(Ni, Co, Mn, Al)O_2$ or compounds with a spinel structure having similar compositions to $LiMn_2O_4$. The negative electrode is generally carbon (graphite, coke, and the like) or optionally the spinel $Li_4Ti_5O_{12}$ or a metal forming an alloy with lithium (Sn, Si, and the like).

In order to respond more particularly to the new hybrid and electric motor vehicle or photovoltaic solar markets, the constraints of cost, production volume and power performances are forcing the search for novel electrode active materials.

From this perspective, polymers have already been provided, for example in the documents WO 2009/043729, WO 2009/127674 or EP 1 244 168, as active materials, for their property of conducting electricity, as replacement for or in addition to conventional electron conductors, such as carbon black. They are mainly used for their ease of processing, compared with suspensions of conducting particles, and make it possible to improve the electrical percolation of the electrode active materials.

The polymers most commonly employed are polyanilines, polypyrroles, proton-conducting compounds containing at least one heterocycle with a nitrogen atom, or also polymers exhibiting, on their chain, a component carrying a disulfide bridge.

By way of example, the document U.S. Pat. No. 7,651,647 provides for the use of a mixture of an active material, such as silver vanadium oxide or fluorinated carbon, and of a conducting polymer chosen from polyaniline, polydioxythiophene and their combination, in the manufacture of a positive electrode of an electrochemical cell.

Mention may also be made of the document JP 2008-192452, which describes the use, as electrode active materials, of conducting polymers formed from monomers exhibiting five-membered heteroaromatic rings, in particular polythiophenes carrying TEMPO radicals or derivatives. These polymers are synthesized by grafting the TEMPO unit to the monomers, followed by the polymerization.

However, the use of these grafted polymers in lithium storage batteries is not completely satisfactory. Thus, it requires the joint use of large amounts of conventional electron conductors, such as carbon black, generally between 20% and 70% by weight, in order to make possible the extraction of the electrons from the active material. Furthermore, the addition of such amounts of electron conductors unfortunately takes place to the detriment of the energy density, by weight or volume, of the electrode and renders any industrial application extremely expensive. Finally, the use of additional binders is necessary in order to ensure the adhesion of the polymer material to the current collector and good mechanical strength of the electrode.

Recently, the documents US 2009/181309, US 2009/152509 and US 2005/239917 have provided carbonyl compounds as cathode materials for lithium batteries.

Nevertheless, although these materials are advantageous in terms of energy and power density, they exhibit numerous problems of electron and ion transportation of the electrode, and of chemical, thermal and electrochemical stability of the material. In addition, these materials have an inadequate redox potential.

The present invention is targeted at providing novel compounds which can be used as electrode material for lithium, sodium or potassium storage batteries, preferably lithium storage batteries, and which make it possible in particular to overcome the above-mentioned disadvantages.

More particularly, it relates, according to a first of its aspects, to the use as electrode active material of a compound comprising at least one entity of formula (I):

in which the phenyl group is substituted by one to four substituent(s) R, which are identical or different, chosen from a hydrogen atom, a halogen atom chosen from fluorine, chlorine, bromine or iodine, a —C(=S)—S⁻C⁺ group, an —O⁻C⁺ group, an —S⁻C⁺ group, with C⁺ being an alkali metal cation chosen from $Li^+$, $Na^+$ and $K^+$, preferably $Li^+$, a ($C_1$-$C_{12}$)alkyl radical, a ($C_2$-$C_{12}$)alkenyl radical or a ($C_6$-$C_{14}$)aryl or -heteroaryl radical or it being possible for two vicinal substituents R, if appropriate, to be bonded to one another in order to together form a 3- to 7-membered ring optionally including another heteroatom chosen from N, O or S; in the base or salt state;
and also its tautomeric forms.

Such compounds prove to be particularly advantageous as electrode active material for lithium, sodium or potassium storage batteries, preferably lithium storage batteries.

The use of the compounds according to the invention as electrode active material proves to be advantageous in several respects.

First of all, the electrodes formed according to the invention exhibit good flexibility and lightness, properties which are particularly desired in the context of portable systems.

They exhibit a very good chemical, thermal and electrochemical stability.

They have improved electron and ion transportation properties, in particular in comparison with those employing the carbonyl compounds described in the documents US 2009/181309, US 2009/152509 and US 2005/239917, and also have a high redox potential.

Furthermore, in contrast to conventional electrodes based on pulverulent inorganic insertion materials, the electrodes comprising the compounds of the invention may be formed according to conventional coating or printing techniques or any other technique for processing organic materials in solution (coating techniques such as spin coating, deep coating, spraying or drop casting) or in the molten state (extrusion, injection molding, rotational space molding or extrusion/blow molding technique, and the like).

Other characteristics, alternative forms and advantages of the compounds according to the invention, of their preparation and of their use will more clearly emerge on reading the description, examples and figures which will follow, given by way of illustration and without limitation of the invention.

Compounds of the Invention

As specified above, the compounds according to the invention comprise at least one entity of formula (I):

(I)

in which the phenyl group is substituted by one to four substituent(s) R, which are identical or different, chosen from a hydrogen atom, a halogen atom chosen from fluorine, chlorine, bromine or iodine, a —C(=S)—S⁻C⁺ group, an —O⁻C⁺ group, an —S⁻C⁺ group, with C⁺ being an alkali metal cation chosen from Li⁺, Na⁺ and K⁺, preferably Li⁺, a ($C_1$-$C_{12}$)alkyl radical, a ($C_2$-$C_{12}$)alkenyl radical or a ($C_6$-$C_{14}$)aryl or -heteroaryl radical or it being possible for two vicinal substituents R, if appropriate, to be bonded to one another in order to together form a 3- to 7-membered ring optionally including another heteroatom chosen from N, O or S; in the base or salt state;

and also its tautomeric forms.

In the context of the present invention:

"$C_t$-$C_z$, where t and z may take the values from 1 to 14" denotes a carbon-based chain which may have from t to z carbon atoms, such as a $C_1$-$C_{12}$ carbon-based chain;

a halogen atom denotes a fluorine, a chlorine, a bromine or an iodine;

an alkyl denotes a saturated and linear, branched or cyclic aliphatic group, in particular comprising from 1 to 12 carbon atoms. Mention may be made, as examples, of the methyl, ethyl, propyl, isopropyl, butyl, isobutyl, tert-butyl, cyclohexyl or cyclopentyl groups, and the like;

an alkenyl denotes a mono- or polyunsaturated and linear, branched or cyclic aliphatic group, in particular comprising from 2 to 12 carbon atoms, for example comprising one or more ethylenic unsaturations. Mention may be made, as examples, of the ethylene, 1-methylethylene, propylene, cyclohexadienyl or phenyl groups, and the like;

an aryl denotes a mono-, bi- or tricyclic aromatic group comprising between 6 and 14 carbon atoms. Mention may be made, as examples of aryl groups, of the phenyl or naphthyl groups, and the like;

a heteroaryl denotes a 5- to 14-membered mono-, bi- or tricyclic aromatic heterocyclic group containing from 1 to 8 heteroatoms chosen from oxygen, sulfur and nitrogen. Mention may be made, as examples of heteroaryl groups, of the pyridine, pyrazine, pyrimidine, pyrazol, oxadiazol, thiazol, imidazol, benzothiophene, quinoline or indol groups and the like;

a 3- to 7-membered ring denotes a 3- to 7-membered unsaturated or saturated, nonaromatic, cyclic group optionally comprising one or more heteroatoms chosen from oxygen, sulfur and nitrogen. Mention may be made, as examples of 3 to 7-membered rings, of the cyclopropyl, cyclopropenyl, cyclobutyl, cyclobutenyl, cyclopentyl, cyclopentenyl, cyclohexyl, azetidinyl, pyrrolidinyl, piperidinyl, morpholinyl, thiomorpholinyl, piperazinyl, homopiperazinyl, dihydrooxazolyl, dihydrothiazolyl, dihydroimidazolyl, dihydropyrrolyl or tetrahydropyridinyl groups, and the like.

The present invention also relates to the tautomeric forms of the compounds comprising an entity of the formula (I) according to the invention.

The term "a tautomeric form" is understood to mean a constitutional isomer, the structure of which differs in the position of an atom, for example a hydrogen atom, and of one or more multiple bonds. Two tautomeric forms are capable of easily and reversibly converting into one another.

The compounds comprising at least one entity of formula (I) may exist in the state of bases or salts. Such salts also come within the invention.

For example, the salts may be salts with an alkali metal or alkaline earth metal cation or salts of transition metals, such as, for example, Li/Na alkoxide, Li/Na sulfonate, Li/Na dialkylamide, and the like. Organic cation salts, such as ammonium, phosphonium or sulfonium salts, may also be concerned.

According to a particularly preferred embodiment, the compounds comprising at least one entity of formula (I) are chosen from the compounds of formula (II):

(II)

in which:

C⁺ is an alkali metal cation chosen from Li⁺, Na⁺ and K⁺, preferably Li⁺;

at least one of the substituents $R_1$, $R_2$, $R_3$, $R_4$ or $R_5$ represents a —C(=S)—S⁻C⁺ group, the others, which are identical or different, representing a group R chosen from a hydrogen atom, a halogen atom chosen from fluorine, chlorine, bromine or iodine, a —C(=S)—S⁻C⁺ group, an —O—C⁺ group, an —S⁻C⁺ group, C⁺ being as defined above, a ($C_1$-$C_{12}$)alkyl radical, a ($C_2$-$C_{12}$)alkenyl radical or a ($C_6$-$C_{14}$)aryl or -heteroaryl radical or it being possible for two vicinal substituents R, if appropriate, to be bonded to one another in order to together form a 3- to 7-membered ring optionally including another heteroatom chosen from N, O or S;
in the base or salt state;
and also its tautomeric forms.

According to one of its aspects, the present invention more particularly relates to compounds of the following formula (IIa):

in which:
at least one of the substituents $R_1$, $R_2$, $R_3$, $R_4$ or $R_5$ represents a —C(=S)—SLi group, the others, which are identical or different, representing a group R chosen from a hydrogen atom, a halogen atom chosen from chlorine, bromine or iodine, a —C(=S)—SLi group, an —OLi group, an —SLi group, a $(C_1$-$C_{12})$alkyl radical, a $(C_2$-$C_{12})$alkenyl radical or a $(C_6$-$C_{14})$aryl or -heteroaryl radical or it being possible for two vicinal substituents R, if appropriate, to be bonded to one another in order to together form a 3- to 7-membered ring optionally including another heteroatom chosen from N, O or S;
in the base or salt state;
and also its tautomeric forms.

Preferably, in the compounds according to the invention, $R_3$ represents a —C(=S)—S⁻C⁺ group, in which C⁺ denotes an alkali metal cation chosen from Li⁺, Na⁺ and K⁺, preferably Li⁺ and $R_1$, $R_2$, $R_4$ and $R_5$, which are identical or different, represent a substituent R as defined above.

According to a specific embodiment, R represents a hydrogen atom, a —C(=S)—S⁻C⁺ group, an —O—C⁺ group or an —S⁻C⁺ group, with C⁺ being an alkali metal cation chosen from Li⁺, Na⁺ and K⁺, preferably Li⁺.

Preferably, R represents a hydrogen atom.

More particularly, the compound bislithium 1,4-benzenebisdithioate of formula:

or its tautomeric form may be concerned.

The products comprising at least one entity of formula (I) as defined above may be prepared by the general methods known to a person skilled in the art.

Furthermore, the compounds of formula (II) according to the invention may be prepared according to the preparation process comprising at least:

(a) the reaction of lithium, sodium or potassium ethoxide with sulfur, and
(b) bringing the reaction mixture obtained on the conclusion of stage (a) into contact with a compound of formula (III):

in which:
at least one of the substituents $R_1$, $R_2$, $R_3$, $R_4$ or $R_5$ represents a $CH_2$—Cl group, the others, which are identical or different, representing a group R chosen from a hydrogen atom, a halogen atom chosen from fluorine, chlorine, bromine or iodine, a —$CH_2$—Cl group, an —O⁻C⁺ group, an —S⁻C⁺ group, with C⁺ being a cation chosen from Li⁺, Na⁺ and K⁺, a $(C_1$-$C_{12})$alkyl radical, a $(C_2$-$C_{12})$alkenyl radical or a $(C_6$-$C_{14})$aryl or -heteroaryl radical or it being possible for two vicinal substituents R, if appropriate, to be bonded to one another in order to together form a 3- to 7-membered ring optionally including another heteroatom chosen from N, O or S;
under conditions favorable to the formation of the compound of formula (II).

According to a specific alternative form of this process, stage (a) of the process is carried out at a temperature of between 25° C. and 150° C. for a period of time varying from 1 hour to 48 hours.

Of course, it is up to a person skilled in the art to adjust the synthesis conditions in order to obtain the compounds according to the invention.

The compounds according to the invention are generally obtained in the form of a solid which lends itself to use as is or, for example, in solution.

Electrode Active Material

As specified above, the compound according to the invention is particularly advantageous as electrode active material.

The term "electrode active material" is understood to mean, within the meaning of the invention, a material for insertion/deinsertion of a cation C⁺ (Li⁺, Na⁺ or K⁺) of an electrode of an electrochemical generator. More particularly, the active material of the positive electrode is capable of releasing C⁺ ions at the time of the charging and of incorporating C⁺ ions at the time of the discharging of the electrochemical generator. Conversely, the active material of the negative electrode is capable of incorporating C⁺ ions at the time of the charging and of releasing C⁺ ions at the time of the discharging of the electrochemical generator.

Thus, the present invention relates to the use of a compound as defined above as electrode active material.

According to another of its aspects, the invention also relates to an electrode active material comprising at least one compound as defined above.

The electrode material may be prepared in the form of a dispersed powder or in solution.

The electrode material may comprise a compound or mixture of compounds according to the invention. It may comprise, in addition to said compound or compounds of the invention, one or more additional compounds conventionally employed, such as, for example, a conducting additive or binder.

Advantageously, this material is immobilized at the electrode.

Electrode

According to yet another of its aspects, the invention relates to an electrode formed in all or part of an electrode material as described above.

It is more particularly targeted at an electrode formed in all or part of an active material comprising at least one compound as defined above and at least one electron-conducting additive.

Preferably, the electrode material represents from 10% to 95% by weight of the total weight of the electrode, in particular more than 40% by weight and more particularly from 40% to 80% by weight, with respect to the total weight of said electrode.

An electrode according to the invention may be used as positive electrode or as negative electrode, in particular of a lithium generator.

Conventionally, an electrode according to the invention may comprise a current collector to which said electrode active material is applied, in particular via the techniques expanded upon below.

For example, aluminum or stainless steel may be used as current collector for a positive electrode and copper, nickel or steel, processed to give a cut foil, a metal foam or a sheet of rolled foil, for example, may be used as current collector for a negative electrode.

Advantageously, an electrode according to the invention may be devoid of current collector.

According to a specific embodiment, the electrode may additionally comprise one or more electron-conducting additive(s).

Said electron-conducting additive or additives may be chosen from carbon fibers, carbon black, carbon nanotubes, graphene and their analogues.

According to a preferred embodiment, said electron-conducting additive or additives may be present in an amount of less than or equal to 60% by weight, with respect to the total weight of said electrode, preferably of less than or equal to 40% by weight and more particularly of less than or equal to 20% by weight, with respect to the total weight of said electrode.

According to a specific embodiment, the electrode may be devoid of electron-conducting additive.

According to another specific embodiment, the electrode may additionally comprise one or more binder(s).

Such binders may advantageously be chosen from fluorinated binders, in particular from polytetrafluoroethylene or polyvinylidene fluoride, polymers derived from carboxymethyl cellulose, polysaccharides and latexes, in particular of styrene-butadiene rubber (SBR) type.

According to a preferred embodiment, said binder or binders may be present in an amount of less than or equal to 40% by weight, with respect to the total weight of the electrode, preferably of less than or equal to 20% by weight, in particular of less than or equal to 10% by weight and more particularly of less than or equal to 5% by weight, with respect to the total weight of the electrode.

In particular, an electrode according to the invention may comprise less than 40% by weight of fluorinated binders, in particular less than 20% by weight of fluorinated binders, with respect to the total weight of the electrode.

According to a specific alternative embodiment, an electrode according to the invention is devoid of binder.

In addition, an electrode may comprise other additives commonly employed for storage battery electrodes.

Electrode Preparation Process

An electrode according to the invention may be prepared according to different techniques.

According to a first alternative embodiment, the electrode according to the invention may be formed by a preparation process comprising at least the stages consisting in:

(i) having available a mixture formed of at least one compound as defined above, of a liquid phase, in particular comprising one or more organic or aqueous solvents, and optionally of one or more electron-conducting additive(s) and/or binder(s), and (ii) depositing said mixture from stage (i) by coating or by a printing technique on a base substrate or by extrusion or by corolling.

The dispersion of stage (i), when it is aqueous, may also comprise a thickener, for example of carboxymethyl cellulose or hydroxypropyl methylcellulose type, and/or a surfactant and/or a salt (for example LiOH). Such a dispersion is also commonly known as "ink". The ink may, for example, be deposited according to stage (ii) on a current collector, such as a metal foil, for example made of aluminum or of copper. The deposition of the ink may, for example, be carried out by flexographic printing, photogravure, screen printing, inkjet printing or spraying. A person skilled in the art is in a position to adjust the conditions under which these various techniques are carried out.

As regards the base substrate, it may be a polymeric film of polyethylene or polypropylene type. Stage (ii) is then followed by a subsequent stage (iii) of detaching said polymeric film, in order to form a self-supported electrode.

According to a second alternative embodiment, an electrode in accordance with the invention may be formed by in situ electropolymerization in solution. Thus, a polymeric layer formed in all or part of entities of formula (I) according to the invention may be generated by electropolymerization of monomers functionalized by entities of formula (I). This electrode may be connected directly to a current collector, such as, for example, an aluminum, nickel, copper, steel or carbon foil, if appropriate in the presence of additional electron conductors.

The invention thus relates, according to another of its aspects, to a process for the preparation of an electrode as defined above, comprising the formation of a polymer by in situ electropolymerization on a current collector of monomers functionalized by entities of formula (I) as described above.

The monomers to be functionalized may be chosen in particular from the family of the pyrrols, thiophenes, fluorenes, carbazols, anilines, phenylenes, isothionaphthenes, acetylenes, phenylene-vinylenes and their mixtures.

According to a particularly preferred alternative form, the electropolymerization takes place directly within a lithium electrochemical cell, for example a lithium electrochemical cell. In this configuration, the electropolymerization takes place during the first charging (or discharging) cycle of the cell and the electrode is formed in situ on the collector of the positive (or negative respectively) electrode.

More particularly, the process for the formation of the electrode by in situ electropolymerization may comprise at least the stages consisting in:

(i) introducing said monomers functionalized by entities of the formula (I) in the powder form into the electrolyte of a lithium, sodium or potassium electrochemical cell or dissolving said functionalized monomers in the electrolyte of a lithium, sodium or potassium electrochemical cell; and (ii) carrying out at least one charging cycle of the cell in order to form a positive electrode or at least one discharging cycle of the cell in order to form a negative electrode.

In the specific case of a lithium electrochemical cell, the electrolyte solution may be chosen from the electrolytes conventionally employed for lithium batteries, through which the $Li^+$ cations have the possibility of migrating. The electrolyte may, for example, be composed of a salt comprising at least the $Li^+$ cation. The salt is, for example, chosen from $LiClO_4$, $LiAsF_6$, $LiPF_4$, $LiBF_4$, $LiR_FSO_3$, $LiCH_3SO_3$, $LiN(R_FSO_2)_2$ or $LiN(R_FSO_2)_3$; $R_F$ being chosen from a fluorine atom and a perfluoroalkyl group comprising between 1 and 8 carbon atoms. The salt is preferably dissolved in a polar aprotic solvent, such as ethylene carbonate, propylene carbonate, dimethyl carbonate or ethyl methyl carbonate, and it may be supported by a separator element positioned between the first and second electrodes, the separator element then being impregnated with electrolyte.

Other alternative embodiments of an electrode according to the invention can also be envisaged, in particular:

by employing the compounds of the invention in solution: dissolution of the active material according to the invention in a solvent, optionally in the presence of additional electron conductors, and deposition of the solution by a conventional technique, for example chosen from the printing (flexographic printing, photogravure, screen printing, inkjet printing, spraying, and the like), drop casting, dip coating or spin coating techniques. Use in solution facilitates the deposition on flexible collectors of the polymer type with a metal deposit or carbon-based fabrics; or also by the use of the compounds of the invention in the molten state: injection molding, extrusion, rotational molding, for example, optionally in the presence of additional electron conductors. In the case of the extrusion, the extrudate will exist in the form of a rod, which will be applied to the current collector by compression (isostatic press, calendering and the like), or preferably in the form of a film, which will be deposited in the molten state directly on an electric conducting collector (Al, Ni, Cu, steel, carbon, and the like).

Lithium, Sodium or Potassium Storage Battery

As mentioned above, the present invention relates to a lithium, sodium or potassium storage battery comprising an electrode according to the invention.

Preferably, it is a lithium storage battery.

It may be a lithium-ion, lithium-polymer, lithium-sulfur, lithium-air or supercapacitor battery and preferably a lithium-ion battery.

The remainder of the battery may be formed according to conventional methods.

Generally, lithium-ion batteries exhibit an architecture with two electrodes (a positive electrode and a negative electrode), both coated onto an electric conducting current collector, which are positioned on either side of an organic or inorganic separator. The two techniques for assembling this architecture which are currently the most widely used are coiling (winding the various constituents in a cylindrical or prismatic geometry) and stacking (layer by layer stacking of the various elements). Of course, other assembling techniques for forming a battery can be envisaged, such as printing techniques.

The electrode according to the invention may constitute the positive electrode or the negative electrode of the battery. Preferably, it will constitute the negative electrode.

In the text, the expressions "of between . . . and . . . " and "ranging from . . . to . . . " and "varying from . . . to . . . " are equivalent and are intended to mean that the limits are included, unless otherwise mentioned.

Unless otherwise mentioned, the expression "comprising a(n)" should be understood as "comprising at least one".

The invention will now be described by means of the following figures and examples, given, of course, by way of illustration and without limitation of the invention.

FIGURES

FIG. 1: Cyclic voltammetry curves of $BBDTLi_2$: in solution on Pt electrode (2 mm) (FIG. 1A) and on glassy carbon (3 mm) (FIG. 1B)

EXAMPLES

Example 1

Preparation of bislithium 1,4-benzenebisdithioate ($BBDTLi_2$)

A solution of lithium ethoxide is prepared by addition of 10 mL of anhydrous ethanol to 0.16 g of lithium metal in a dropping funnel.

This solution is subsequently added dropwise to 5.86 g of crystalline sulfur in 90 mL of anhydrous ethanol.

The reaction mixture is maintained at reflux for approximately 2 hours.

One equivalent of α,α'-dichloro-p-xylene (1 g) is subsequently added in the solid form to the reaction mixture and brought to reflux for 20 hours.

After cooling to ambient temperature, the crude mixture is filtered, in order to remove the excess sulfur, and then the filtrate is concentrated under reduced pressure and again filtered.

The solution is subsequently evaporated to dryness in order to give a red solid.

The solid is copiously washed with toluene, cyclohexane and dichloromethane.

The crude residual solid is purified by slow recrystallization at ambient temperature from an ether/cyclohexane mixture.

The structure of the bislithium 1,4-benzenebisdithioate compound obtained is characterized by single-crystal X-ray diffraction. The crystal data obtained are given in detail in table 1 below.

TABLE 1

| | |
|---|---|
| Compound | Bislithium 1,4-benzenebisdithioate (BBDTLi$_2$) |
| Empirical formula | C$_8$H$_{16}$Li$_2$O$_6$S$_4$ |
| Atomic weight | 350.33 |
| Temperature | 150(2) K |
| Wavelength | 0.71073 A |
| Crystal system | Monoclinic |
| Space group | P 1 21/c 1 |
| Unit cell dimensions | a = 8.0373(5) A    alpha = 90° |
| | b = 16.5938(11) A  beta = 104.367(8)° |
| | c = 6.0809(6) A    gamma = 90° |
| Volume, Z | 785.65(10) A$^3$, 2 |
| Density (calculated) | 1.481 g/cm$^3$ |
| Absorption coefficient | 0.618 mm$^{-1}$ |
| F(000) | 364 |
| Size of the crystal | 0.40 × 0.05 × 0.02 mm |

Example 2

Cyclic Voltammetry of the BBDTLi$_2$ in Solution

A 1 mM solution of bislithium 1,4-benzenebisdithioate in acetonitrile (AN) containing 0.1 M tetrabutylammonium hexafluorophosphate (TBAPF$_6$) is prepared. The cyclic voltammetry curves are measured by scanning the potential between 1 and 4 V vs Li$^+$/Li$^0$ at a rate of 0.1 V/s.

Figure 1A:
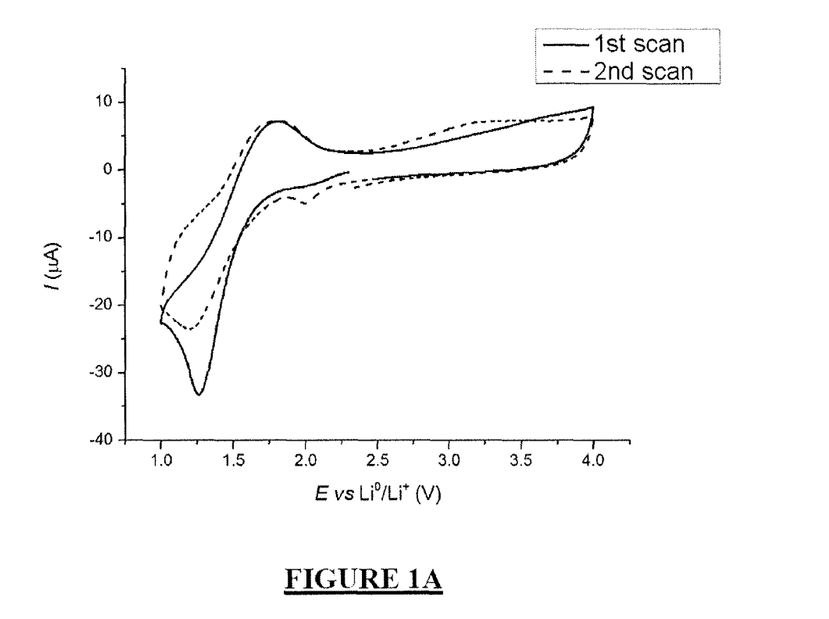
Figure 1B:
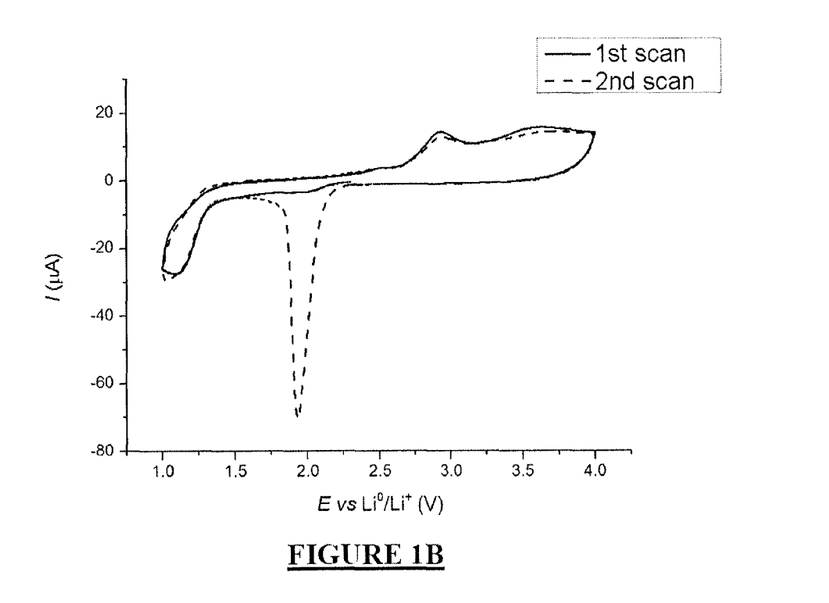

The variation in the electrical potential applied to the platinum or glassy carbon electrode is measured (FIGS. 1A and 1B respectively).

With regard to the platinum electrode (2 mm) (FIG. 1A), the process of reversible reduction of the bislithium 1,4-benzenebisdithioate is observed at a potential of 1.25 V vs Li$^+$/Li$^0$ (solid line curve) and then the appearance of a new redox process in the 2$^{nd}$ scan (dotted line curve) is detected at 1.99 V.

With regard to the glassy carbon electrode (3 mm) (FIG. 1B), the irreversible reduction of the bislithium 1,4-benzenebisdithioate is measured at a potential of 1.09 V vs Li$^+$/Li$^0$ (solid line curve). With regard to this electrode, the electrogeneration of a new product in the 2$^{nd}$ scan (dotted line curve) is observed at a potential of 1.93 V vs Li$^+$/Li$^0$.

Example 3

Preparation of an Electrode

An electrode having the composition BBDTLi$_2$:SuperP:Binder=40:40:20 (as % by weight) is prepared according to the following stages.

40% of BBDTLi$_2$ and 40% of SuperP are ground in the presence of cyclohexane. The cyclohexane is subsequently evaporated at ambient temperature for 30 minutes.

20% of polyvinylidene difluoride binder (12% PVDF solution) and N-methylpyrrolidone (NMP) are subsequently added in order to form an ink.

This ink is coated with a thickness of 200 vim onto a copper current collector and is then dried in an oven at 55° C. for 24 hours.

Electrodes with a diameter of 14 mm are cutout using a hollow punch and then dried in a Büchi oven at 80° C. for 48 hours.

Example 4

Manufacture of a Button Half-Cell

In order to determine the electrochemical performance of the electrode material according to the invention, a battery of "button cell" type is produced with:

a lithium metal negative electrode (1 M LiTFSI in TEGDME:diox=1:1 (% by volume));
a positive electrode composed of a BBDTLi$_2$:SuperP:Binder=40:40:20 (% by weight) composition, comprising the compound of the invention prepared according to example 1 deposited on copper; and
two separators based on polyolefins.

Figure 2A:
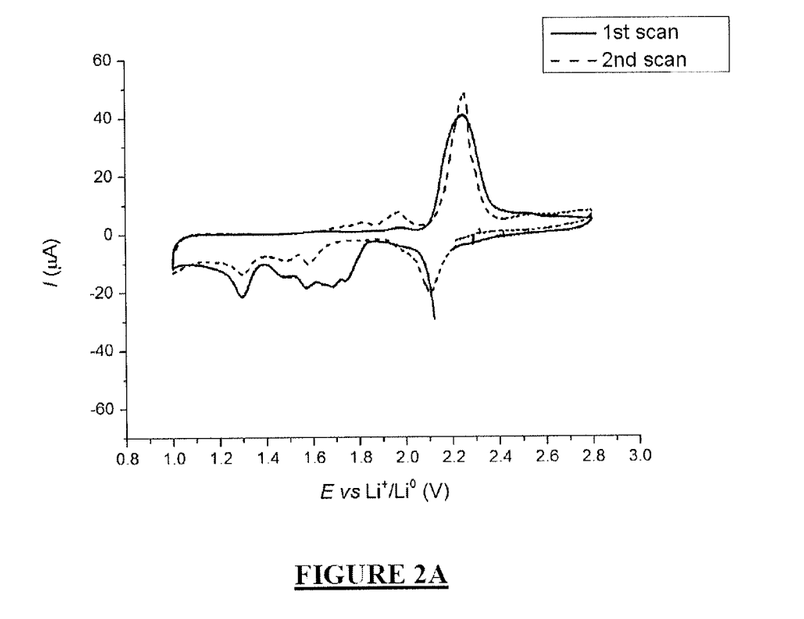
FIG. 2: Cyclic voltammetry curves of $BBDTPLi_2$ in a button cell
Figure 2B:
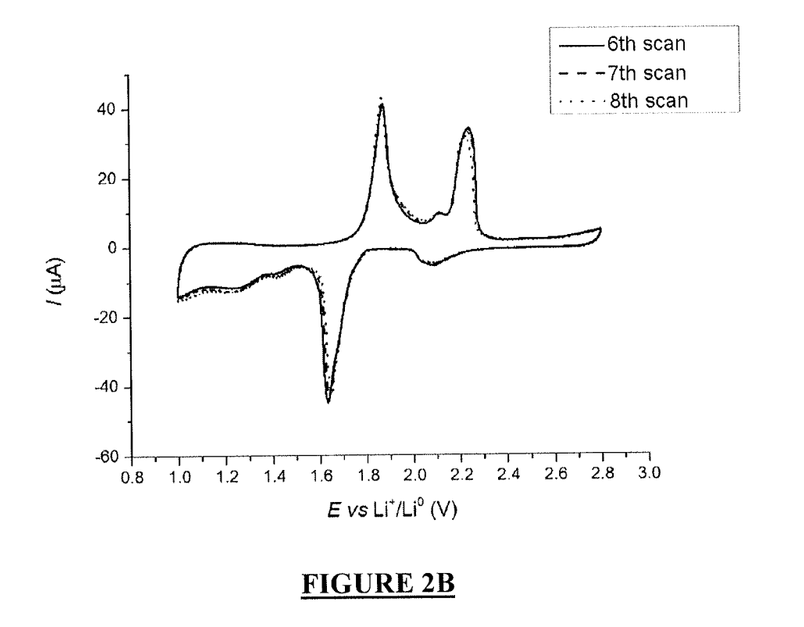

The variation in the electrical potential during the cycles is measured (FIG. 2A (1$^{st}$ and 2$^{nd}$ scans) and FIG. 2B (from the 6$^{th}$ to the 8$^{th}$ scan)).

In the first scan, the existence of several reduction processes is observed between 1.2 and 1.8 V vs Li$^+$/Li$^0$ and, from the 2$^{nd}$ cycle, the appearance is observed of new electrochemical signatures, for subsequently generating a very stable system (FIG. 2B), characterized by a reduction process at a potential of 1.64 V vs Li$^+$/Li$^0$ and two oxidation processes at 1.86 and 2.23 V vs Li$^+$/Li$^0$.

Figure 3:
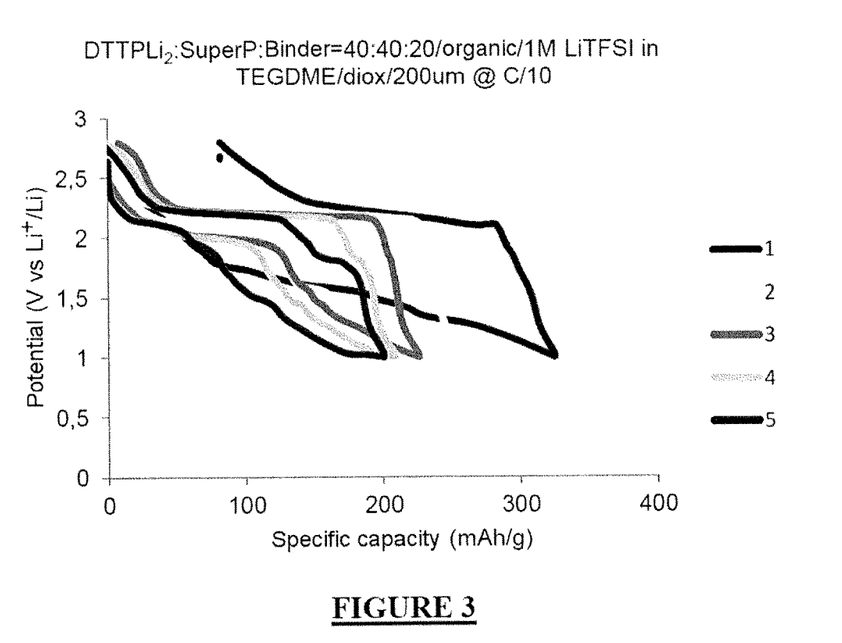
FIG. 3: Capacity-potential curves of $BBDTLi_2$ in a button cell
Figure 4:
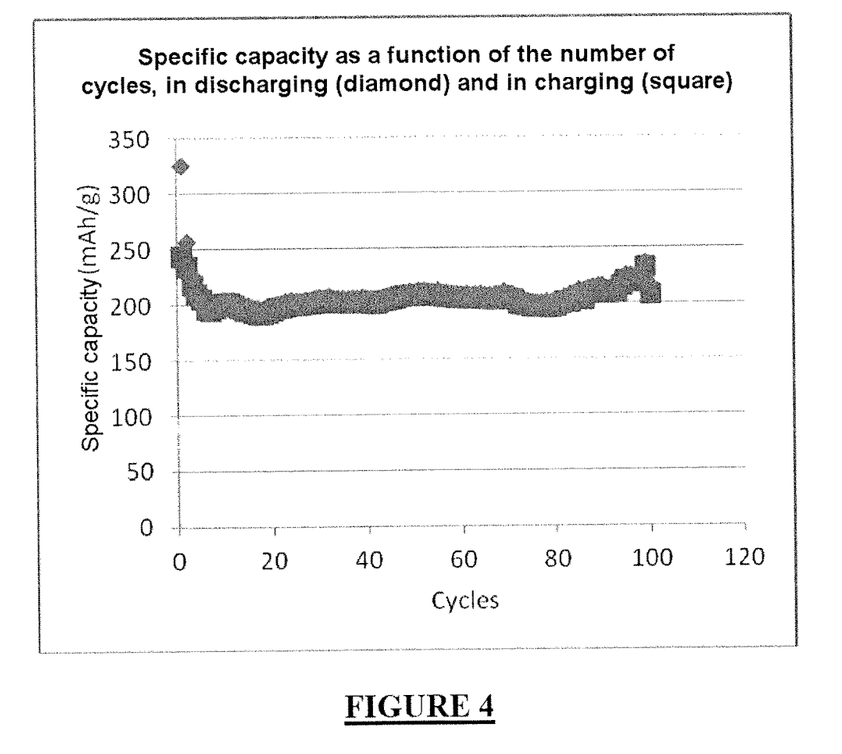
FIGS. 4 to 6: Cyclic curves of $BBDTLi_2$ under different conditions

The specific capacity as a function of the electrical potential is also measured (FIG. 3). In the first cycle, a capacity of 320 mAh·g$^{-1}$, which is greater than the theoretical capacity of BBDTLi$_2$ (Q$_{th}$=221 mAh·g$^-$), is measured. The specific capacity then decreases and stabilizes at ~200 mAh·g$^{-1}$ after five cycles (FIG. 4).

Figure 5:
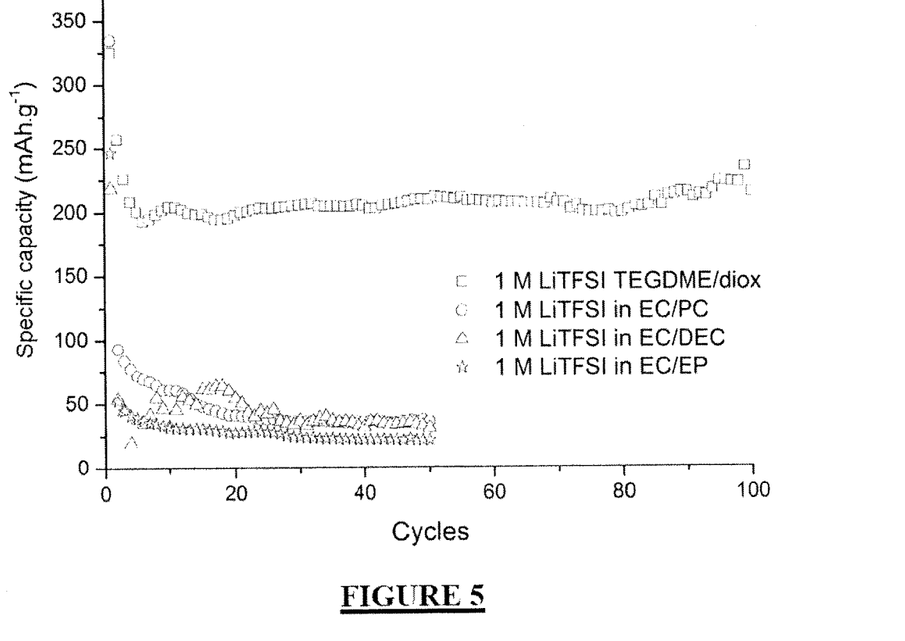
Figure 6:
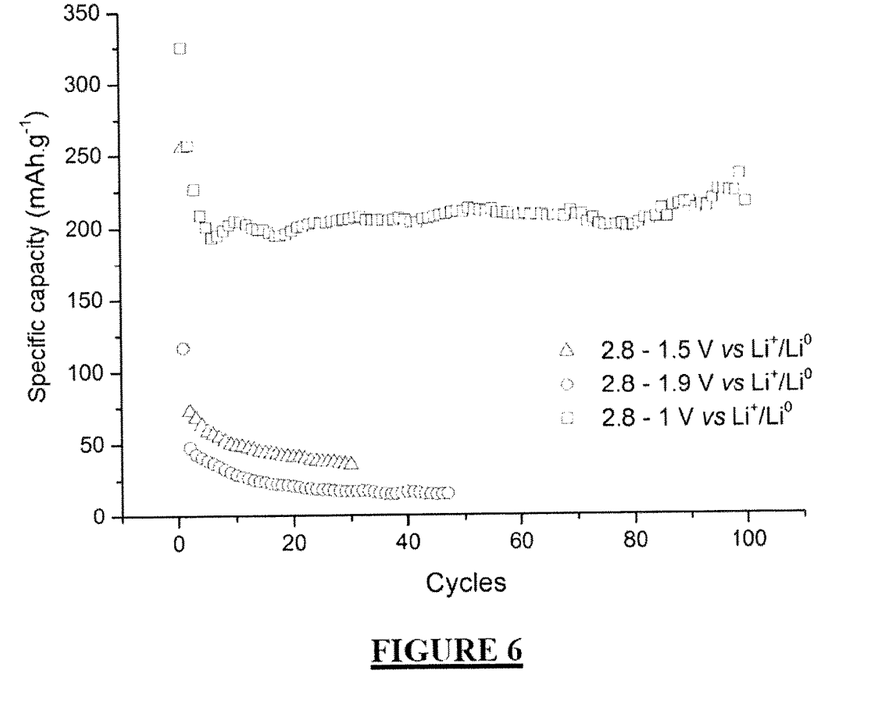

The cycling behavior of the electrogenerated material was measured under various conditions, either, on the one hand, by changing the solvent (FIG. 5, from 1 to 1.8 V), or by replacing the mixture of ethers with carbonate mixtures, or, on the other hand, in different potential ranges (FIG. 6).

Figure 7:
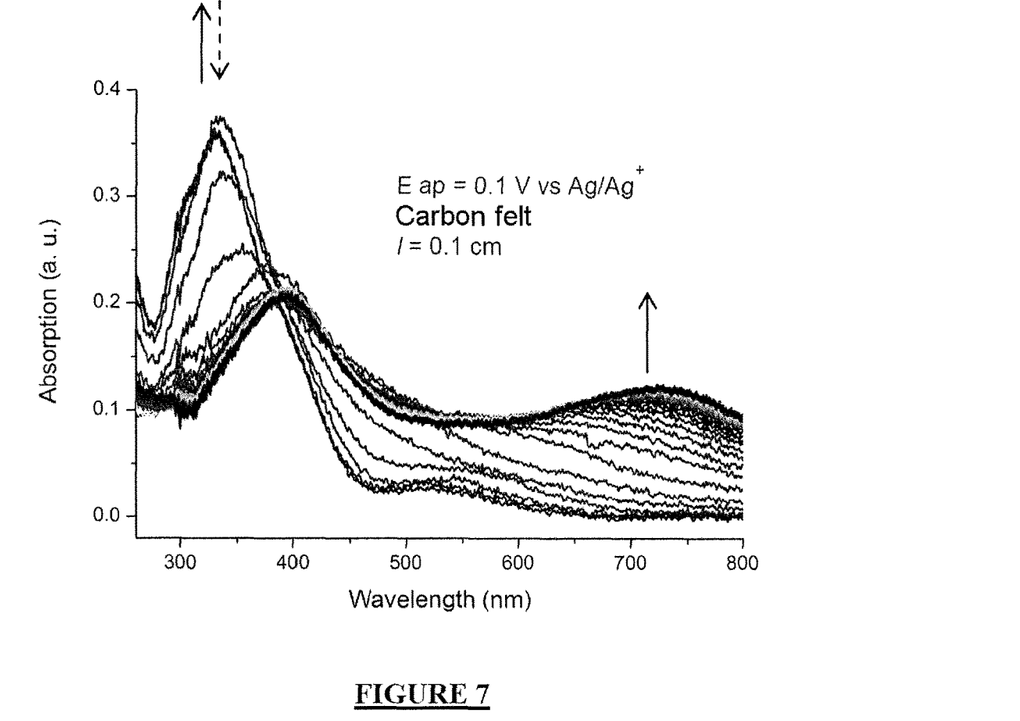
FIG. 7: UV-visible spectrum recorded during the electrolysis of $BBDTLi_2$

In order to understand the nature of the material electrogenerated in situ during the cycling of the BBDTLi$_2$, spectroelectrochemical studies were carried out (FIG. 7).

The exhaustive electrolysis of the BBDTLi$_2$ in 0.1 M tetrabutylammonium hexafluorophosphate in acetonitrile (TBAPF$_6$/AN), monitored by UV-visible spectroscopy, results in major spectroscopic changes, such as the decrease in intensity of the band at ~340 nm, accompanied by the emergence of new bands in the near IR.

Example 5

Comparison of the Performance of BBDTLi$_2$ with Dilithium Terephthalate TPLi$_2$ (not in Accordance)

Preparation of Dilithium Terephthalate (TPLi$_2$)

1 g of terephthalic acid is dispersed in 50 mL of a 1/1 by volume ethanol/water mixture and then 0.44 g of lithium carbonate is added.

The solution is heated in an autoclave at 110° C. for 48 hours. The precipite is subsequently separated by centrifuging, washed with ethanol and then dried at 50° C. 1 g of white powder is obtained.

Electrochemical Performance of TPLi$_2$

The electrochemical characterization of TPLi$_2$ is carried out according to the procedure described in the preceding examples 3 and 4, except for the fact that the electrolyte used is a solution of LiPF$_6$ (1M) in a carbonate mixture and that the charging conditions are C/50.

Figure 8:
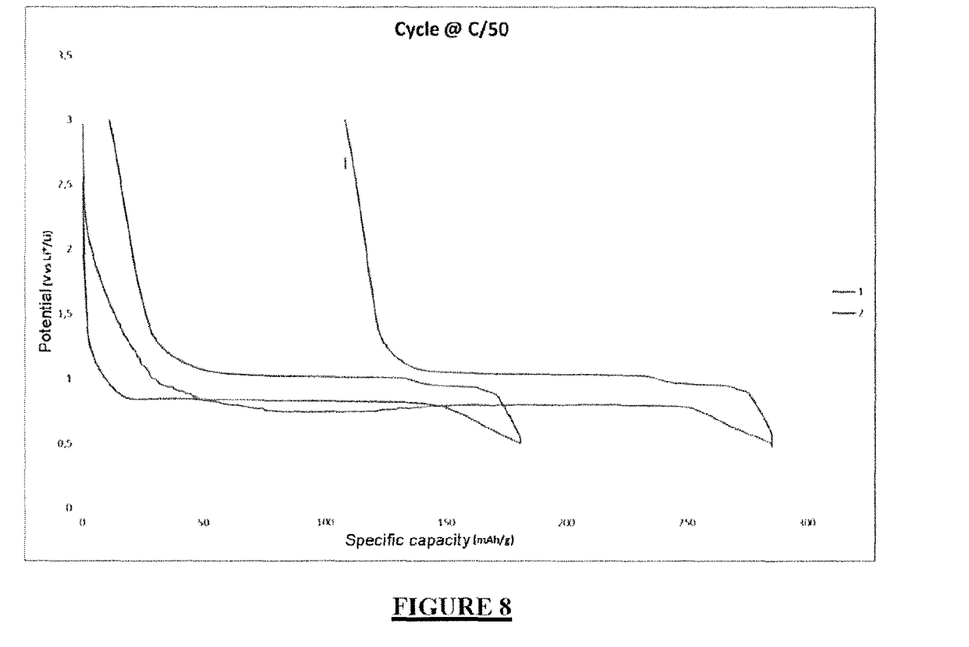
FIG. 8: Capacity-potential curves of $TPLi_2$ (not in accordance with the invention) in a button cell

FIG. 8 shows the change in the potential as a function of the specific capacity during the first two cycles under C/50 conditions. These curves show a very significant decrease in the capacity during the first two cycles.

Figure 9:
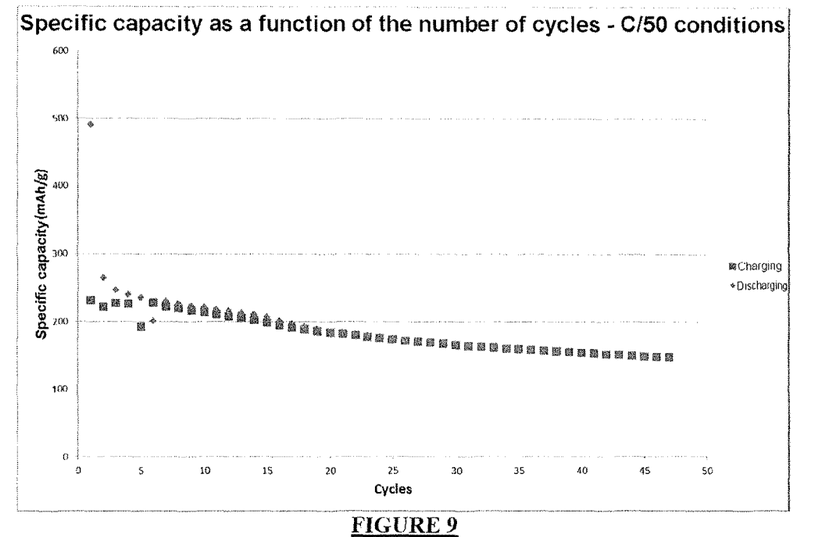
FIGS. 9 and 10: Cyclic curves of $TPLi_2$ (not in accordance with the invention) under different conditions
Figure 10:
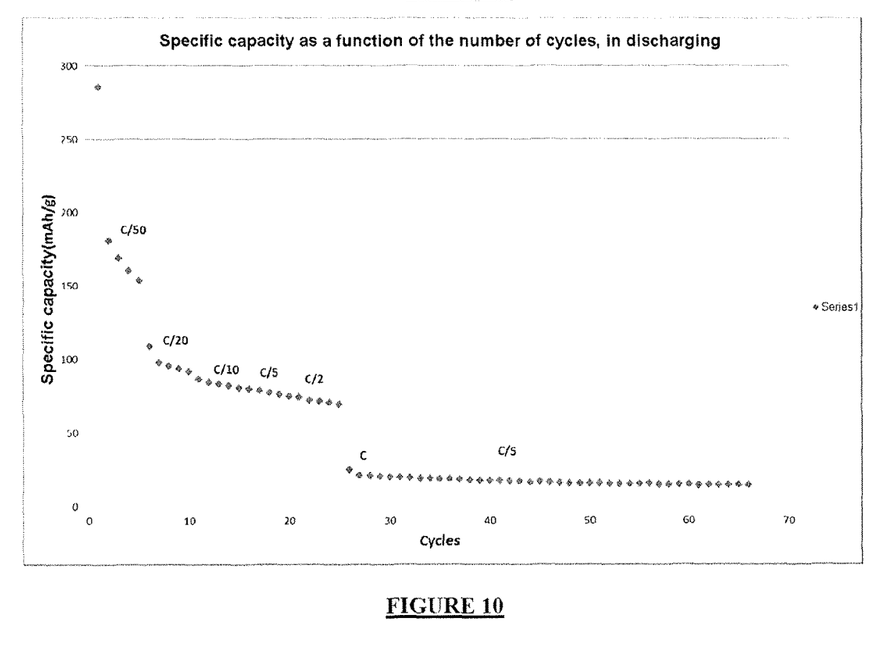

The measurement of the specific capacity as a function of the number of cycles, under C/50 conditions (FIG. 9), shows a constant decrease in the capacity with the number of cycles. Furthermore, it may be noted, from FIG. 10, which represents the specific capacity as a function of the number of cycles, under discharging conditions, that the capacities under C/50 conditions are greater than those under C/10 conditions.

Comparison of the Performances of BBDTLi$_2$ and TPLi$_2$

Figure 11:
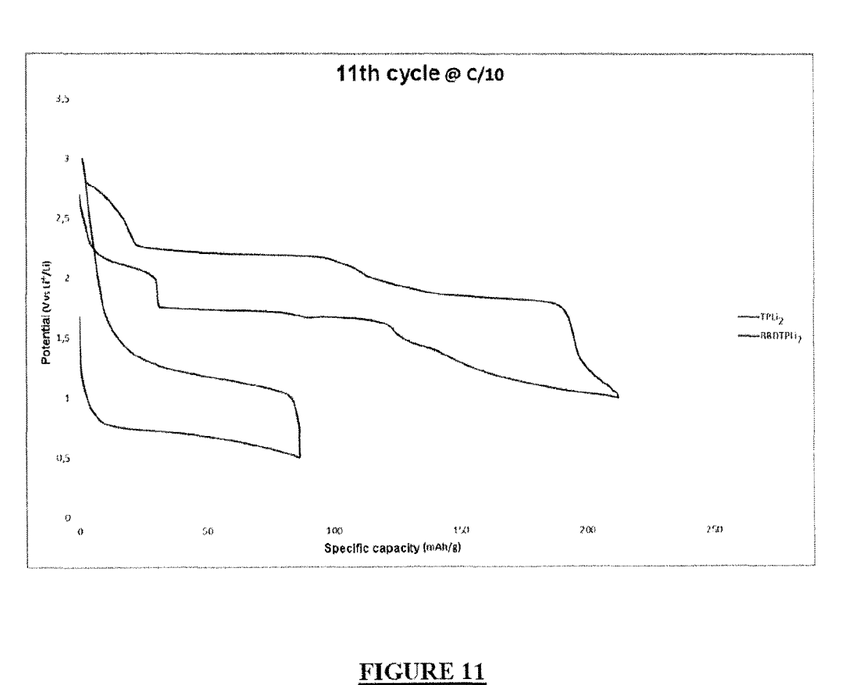
FIG. 11: Comparison of the capacity under C/10 conditions for $BBDTLi_2$ and $TPLi_2$

The change in the potential as a function of the specific capacity, during the 11$^{th}$ cycle under C/10 conditions, for BBDTLi$_2$ and TPLi$_2$, is represented in FIG. 11.

Figure 12:
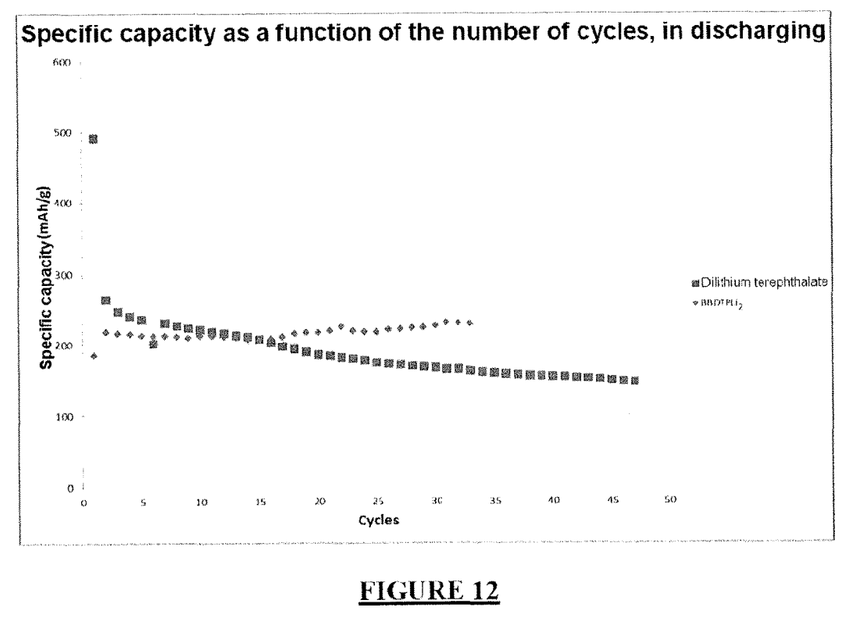
FIG. 12: Comparison of the capacity as a function of the number of cycles for $BBDTLi_2$ (C/10 conditions) and $TPLi_2$ (C/50 conditions).

Likewise, in FIG. 12, the curves and respectively represent the change in the specific capacity, as a function of the number of cycles, under discharging conditions, for the battery with TPLi$_2$ and the battery with BBDTLi$_2$, under C/50 conditions for the first and under C/10 conditions for the second.

The performances of the batteries employing BBDTLi$_2$ in accordance with the invention and TPLi$_2$ as active material of the positive electrode are summarized in the following table 1.

TABLE 1

| Active material of the positive electrode | Voltage[1] (V vs Li$^+$/Li) | Capacity under C/10 conditions[2] | Cycling behavior | Irreversible loss (%)[3] |
|---|---|---|---|---|
| BBDTLi$_2$ (according to the invention) | 2 | 220 | Stable | 35 |
| TPLi$_2$ (prepared by the inventors) | 0.8 | 80 | Loss in performance at each cycle | 60 |

[1]discharge voltage (mean voltage value over the 11$^{th}$ cycle);
[2]capacity in the 11$^{th}$ cycle (C/10 conditions);
[3]loss in discharging/charging capacity in the 1$^{st}$ cycle.

The invention claimed is:

1. An electrode active material comprising at least one compound of formula (IIa):

(IIa)

in which:
at least one of the substituents R$_1$, R$_2$, R$_3$, R$_4$ or R$_5$ represents a —C(=S)—SLi group, the others, which are identical or different, representing a substituent R selected from the group consisting of a hydrogen atom, a halogen atom chosen from chlorine, bromine or iodine, a —C(=S)—SLi group, an —OLi group, an —SLi group, a (C$_1$-C$_{12}$)alkyl radical, a (C$_2$-C$_{12}$) alkenyl radical or a (C$_6$-C$_{14}$)aryl or -heteroaryl radical or it being possible for two vicinal substituents R, if appropriate, to be bonded to one another in order to together form a 3- to 7-membered ring optionally including another heteroatom chosen from N, O or S;
or base, salt, or tautomeric forms thereof.

2. The electrode active material as claimed in claim 1, which is provided in the form of a dispersed powder or in solution in said conducting additive or binder.

3. The electrode active material as claimed in claim 1, wherein R$_3$ in formula (IIa) represents a —C(=S)—SLi group, and R$_1$, R$_2$, R$_4$ and R$_5$, which are identical or different, represent a substituent R as defined above.

4. The electrode active material as claimed in claim 1, wherein the compound is bislithium 1,4-benzenebisdithioate of formula:

or its tautomeric form.

5. An electrode formed in all or part of an electrode active material and at least one electron-conducting additive,
said electrode active material comprising
at least one compound of formula (IIa):

in which:
at least one of the substituents R$_1$, R$_2$, R$_3$, R$_4$ or R$_5$ represents a —C(=S)—SLi group, the others, which are identical or different, representing a substituent R selected from the group consisting of a hydrogen atom, a halogen atom chosen from chlorine, bromine or iodine, a —C(=S)—SLi group, an —OLi group, an —SLi group, a (C$_1$-C$_{12}$)alkyl radical, a (C$_2$-C$_{12}$)alkenyl radical or a (C$_6$-C$_{14}$)aryl or -heteroaryl radical or it being possible for two vicinal substituents R, if appropriate, to be bonded to one another in order to together form a 3- to 7-membered ring optionally including another heteroatom chosen from N, O or S;
or base, salt, or tautomeric forms thereof.

6. The electrode as claimed in claim 5, said electron-conducting additive(s) being selected from the group consisting of carbon fibers, carbon black, carbon nanotubes, graphene and their analogues.

7. The electrode as claimed in claim 5, additionally comprising at least one binder.

8. The electrode as claimed in claim 7, said binder(s) being selected from the group consisting of fluorinated binders, polymers derived from carboxymethyl cellulose, polysaccharides and latexes.

9. The electrode as claimed in claim 5, wherein the compound is bislithium 1,4-benzenebisdithioate of formula:

or its tautomeric form.

10. A lithium, sodium or potassium storage battery, comprising an electrode formed in all or part of an electrode active material,
said electrode active material comprising
at least one compound of formula (IIa):

(IIa)

in which:
at least one of the substituents $R_1$, $R_2$, $R_3$, $R_4$ or $R_5$ represents a —C(=S)—SLi group, the others, which are identical or different, representing a substituent R selected from the group consisting of a hydrogen atom, a halogen atom chosen from chlorine, bromine or iodine, a —C(=S)—SLi group, an —OLi group, an —SLi group, a $(C_1$-$C_{12})$alkyl radical, a $(C_2$-$C_{12})$alkenyl radical or a $(C_6$-$C_{14})$aryl or -heteroaryl radical or it being possible for two vicinal substituents R, if appropriate, to be bonded to one another in order to together form a 3- to 7-membered ring optionally including another heteroatom chosen from N, O or S;
or base, salt, or tautomeric forms thereof.

11. The battery as claimed in claim 10, being a lithium storage battery.

12. The battery as claimed in claim 10, wherein the compound is bislithium 1,4-benzenebisdithioate of formula:

or its tautomeric form.

13. A process for the preparation of an electrode as defined according to claim 5, comprising at least the stages of:
(i) having available a mixture formed:
of at least one of said electrode active material,
of a liquid phase,
of one or more electron-conducting additive(s), and
optionally of one or more binder(s); and
(ii) depositing said mixture from stage (i) by coating or by a printing technique on a base substrate or by extrusion or by corolling.

14. The process as claimed in claim 13, said base substrate being a polymeric film of polyethylene or polypropylene type, said process comprising a subsequent stage (iii) of detaching said polymeric film, in order to form a self-supported electrode.

15. A process for the preparation of an electrode according to claim 5, comprising the formation of a polymer by in situ electropolymerization on a current collector of monomers functionalized by entities of formula (IIa).

16. The process as claimed in claim 15, comprising at least the stages of:
(i) introducing said monomers functionalized by entities of the formula (IIa) in the powder form into the electrolyte of a lithium, sodium or potassium electrochemical cell or dissolving said functionalized monomers in the electrolyte of a lithium, sodium or potassium electrochemical cell; and
(ii) carrying out at least one charging cycle of the cell in order to form a positive electrode or at least one discharging cycle of the cell in order to form a negative electrode.

* * * * *